(12) United States Patent
Ludwinski et al.

(10) Patent No.: US 11,748,421 B2
(45) Date of Patent: Sep. 5, 2023

(54) MACHINE IMPLEMENTED VIRTUAL HEALTH AND BEAUTY SYSTEM

(71) Applicant: L'OREAL, Paris (FR)

(72) Inventors: Celia Ludwinski, Clark, NJ (US); Guive Balooch, Clark, NJ (US); Rafal Pielak, San Francisco, CA (US); Adam Jones, San Francisco, CA (US)

(73) Assignee: L'OREAL, Paris (FR)

( * ) Notice: Subject to any disclaimer, the term of this patent is extended or adjusted under 35 U.S.C. 154(b) by 1063 days.

(21) Appl. No.: 16/241,417

(22) Filed: Jan. 7, 2019

(65) Prior Publication Data

US 2019/0213227 A1 Jul. 11, 2019

Related U.S. Application Data

(60) Provisional application No. 62/614,095, filed on Jan. 5, 2018.

(51) Int. Cl.
| | |
|---|---|
| *G06F 16/9535* | (2019.01) |
| *A45D 44/00* | (2006.01) |
| *A61B 5/00* | (2006.01) |
| *G06N 20/00* | (2019.01) |
| *G06F 3/0482* | (2013.01) |
| *G06Q 30/02* | (2023.01) |
| *G06N 5/04* | (2023.01) |
| *G06Q 30/0601* | (2023.01) |

(52) U.S. Cl.
CPC ....... *G06F 16/9535* (2019.01); *A45D 44/005* (2013.01); *A61B 5/0077* (2013.01); *G06N 20/00* (2019.01); *A45D 2044/007* (2013.01); *G06F 3/0482* (2013.01); *G06N 5/04* (2013.01); *G06Q 30/02* (2013.01); *G06Q 30/0631* (2013.01)

(58) Field of Classification Search
CPC ... G06F 16/9535; G06F 3/0482; G06N 20/00; G06N 5/04; G06N 3/0454; G06N 5/003; G06N 5/025; G06N 7/005; G06N 20/20; G06N 5/022; G06N 20/10; G06Q 30/02; G06Q 30/0631; G16H 10/60; G16H 20/00; G16H 50/20; A45D 44/005; A45D 2044/007; A61B 5/0077
See application file for complete search history.

(56) References Cited

U.S. PATENT DOCUMENTS

| | | | |
|---|---|---|---|
| 2008/0194928 A1* | 8/2008 | Bandic | A61B 5/0082 600/306 |
| 2016/0012194 A1* | 1/2016 | Prakash | G16H 40/40 705/2 |
| 2017/0039344 A1* | 2/2017 | Bitran | G16H 20/10 |
| 2017/0116879 A1* | 4/2017 | Baarman | A61B 5/024 |
| 2017/0270593 A1* | 9/2017 | Sherman | G06N 3/082 |
| 2018/0120132 A1* | 5/2018 | Tanutama | G01D 18/00 |

* cited by examiner

*Primary Examiner* — John T Repsher, III
(74) *Attorney, Agent, or Firm* — Oblon, McClelland, Maier & Neustadt, L.L.P.

(57) ABSTRACT

An apparatus is provided that includes comprising: a processing circuit to accept data indicative at least one health of beauty state of a user; a communication circuit to convey the accepted data to machine learning models and to receive a regimen recommendation from the machine learning models; and a user interface circuit to present the regimen recommendation to the user.

6 Claims, 6 Drawing Sheets

MACHINE IMPLEMENTED VIRTUAL HEALTH AND BEAUTY SYSTEM

CROSS-REFERENCE TO RELATED APPLICATIONS

This application claims the benefit of priority from U.S. Provisional Application No. 62/614,095 filed Jan. 5, 2018, the entire contents of which are incorporated herein by reference.

BACKGROUND

Currently, if a user seeks health and beauty advice, the user may perform a search query to a general information database to location information. For instance, a user may query any number of questions in an Internet search engine (such as Google) and retrieve a list of search results. However, such a result is based strictly on what is available on the Internet and is not based on sensed characteristics of the user.

Additionally, there are some cosmetic devices that are capable of sensing physical characteristics of the user. However, a user may only retrieve the sensed characteristics based on such an appliance when specifically using the appliance or an application dedicated for the appliance.

Therefore, there is a need for an interactive device which is able to manage information received from multiple cosmetic devices which capable of sensing physical characteristics of the user, and utilizing the data to respond user inquiries and track and manage the health, lifestyle, and physical appearance of the user.

SUMMARY

In an embodiment, an apparatus is provided comprising: a processing circuit to accept data indicative at least one health of beauty state of a user; a communication circuit to convey the accepted data to machine learning models and to receive a regimen recommendation from the machine learning models; and a user interface circuit to present the regimen recommendation to the user.

In an embodiment, the apparatus further includes at least one diagnostic device coupled to the processing circuit to provide the data indicative of the health and beauty state.

In an embodiment, the processing circuit is further configured to accept input data indicative of the efficacy of the regimen.

In an embodiment, the input data indicative of the efficacy of the regimen is accepted from the diagnostic device.

In an embodiment, a method is provided comprising: accepting data indicative at least one health of beauty state of a user; conveying the accepted data to machine learning models; receiving a regimen recommendation from the machine learning models; and presenting the regimen recommendation to the user.

DESCRIPTION

Figure 1:
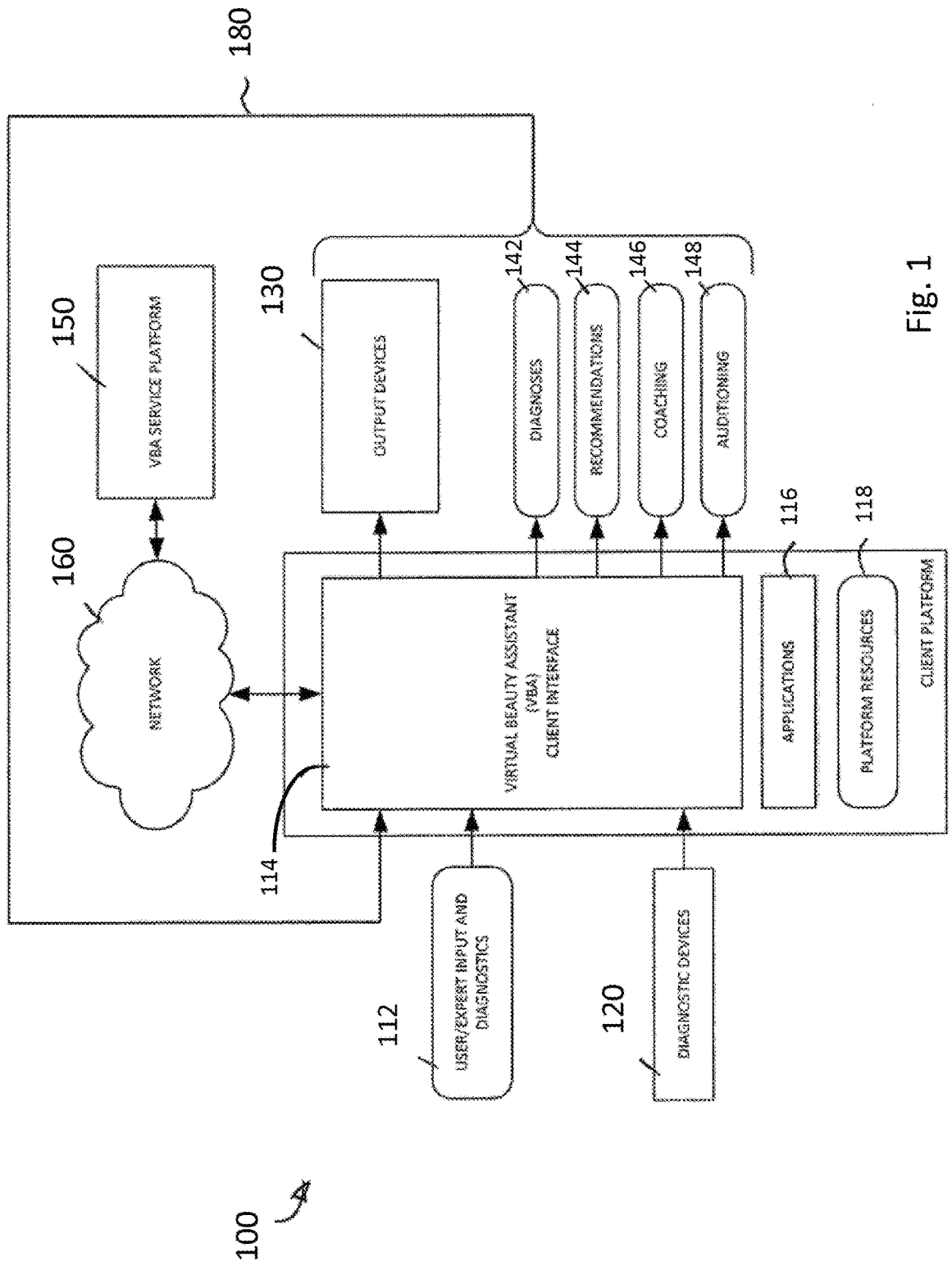
FIG. 1 is a schematic block diagram of an example embodiment of the present general inventive concept.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments. Particular quality or fitness of the examples indicated herein as exemplary is neither intended nor should be inferred.

FIG. 1 is a schematic block diagram of an exemplary virtual beauty assistant (VBA) 100 comprising a VBA client platform 110 and a VBA service platform 150. VBA 100 may be configured to provide, for example, health and beauty assistance to a user in the form of, for example, information provided to output devices 130, recommendations 142, coaching 144, and auditioning 146, based on input data in the form of, for example, user and expert (e.g., a dermatologist or other specialist) input and diagnostics 112 and/or data from various diagnostic devices 120. Whereas, the descriptions that follow relate to the health and beauty domain, those having skill in the art will readily recognize other fields of endeavor in which the invention can be implemented without departing from the spirit and intended scope thereof.

Example VBA 100 accepts user and/or expert input and diagnostics 112. Such input may take the form of, for example, verbal, textual and/or tactile menu-driven information that is analyzed by VBA 100 toward formulating a response. For example, the user may submit a vocal query to VBA 100, e.g., "How can I get rid of the dark circles under my eyes?" VBA 100 may extract relevant parts of speech from the query statement and may formulate a query recognizable by an expert system or other query target, such as a database. VBA 100 may consult data collected from various diagnostic devices 120 to determine whether a user's action or inaction may be contributing to her condition, i.e., the dark circles. For example, one diagnostic device may measure or otherwise surmise the user's sleep patterns, such as by determining how much tossing and turning the user undergoes during sleep time (motion detectors) and/or by detecting snoring sounds over the system microphone. Accordingly, VBA 100 may respond, such as by synthesized speech, "You are getting only 5 hours of sleep per night. Low amounts of sleep have been shown to cause dark circles under the eyes. I recommend that you get 8 hours of sleep per night." Alternatively, such as when it is determined that the user is getting sufficient sleep, or additionally, VBA 100 may respond, "I recommend Product X, which has been shown effective against dark circles under the eyes. Would you like me to order that for you?" Upon a verbal "Yes" from the user, VBA 100 may place an order with a suitable vendor, such as through an appropriate application contained in applications 130. Alternatively, various characteristics about the user may be known to VBA 100, such as through user profile data, and VBA 100 may respond, "I recommend applying Product Y to conceal the dark circles. Would you like me to show you how?" Upon a verbal "Yes" from the user, VBA 100 may instantiate an application from applications 130 that provides a video presentation to the user on how the product should be applied.

VBA 100 may be configured to interact with a variety of "smart" devices for diagnostic devices 120. As those skilled in the health and beauty fields will attest, numerous such devices are commercially available in the health and beauty market. VBA 100 may implement an application programming interface (API) as well as appropriate electrical and mechanical interfaces to operate and communicate with such devices.

One device of diagnostic devices 120 may be a hairbrush equipped with various sensors that monitor hair brushing technique (motion detectors) as well as hair characteristics, such as oiliness/dryness. Upon detecting hair brushing, such as by detecting hair brushing motions, VBA 100 may gather diagnostic data, such as motions attributed to detangling the hair, and may provide recommendations to overcome such tangles. For example, VBA 100 may provide coaching as to how to detangle using an appropriate brushing technique, or may provide a hair care product recommendation, e.g., a conditioner.

Example VBA client platform 110 provides the machine infrastructure by which a user interacts with VBA 100. To that end, VBA client platform 110 may implement a VBA client interface 114 through which the user interacts with VBA 100, e.g., making queries, entering profile and ground truth data, providing feedback on regimen progress, product efficacy and user's product experience, etc. VBA client platform 110 may also include a set of applications 116 that can be instantiated as necessary by VBA client interface 114 and may be equipped with platform resources 118 by which information about the platform may be ascertained (e.g., camera for photographic input, GPS receiver for time and position input, etc.). In certain embodiments, VBA client platform 110 is implemented by a smartphone, tablet computer or other mobile device, although such implementation is not essential to practice the present invention.

VBA service platform 150 may provide services to VBA client platform 110 over, for example, network 150. VBA service platform 150 may be implemented by one or more servers accessible through network 150. Alternatively, VBA service platform 150 and VBA client platform 110 may be collocated in a common device. Services of VBA service platform 150 may be accessible through a VBA client interface 114 and may include machine learning and learned behaviors, database and associated database management system and other services by which VBA output is generated from VBA input.

One or more applications 116 may interact with VBA service platform 150, such as through VBA client interface 114. Example applications 130 include those that instantiate instructional media, e.g., makeup coaching, formulate and submit fabrication orders for cosmetic sets based on a user's skin tone and other characteristics, formulate and submit fabrication orders for specialty cosmetics based on user preferences or a dermatologist's recommendations, and so on. In certain embodiments, one or more applications 130 may reside on a user's mobile device (not illustrated).

Feedback path 180 represents several mechanisms by which VBA 100 implements feedback for purposes of machine learning leading to results tuned to a user's preferences and goals. The efficacy of regimens recommended by VBA 100 can be determined from subsequent user inputs. For example, VBA 100 may recommend a specific wrinkle cream to remove, for example, crow's feet at the corner of a user's eyes. Photographs (images) of the user may be taken over time and VBA 100 may note from image processing that the crow's feet are not being reduced at the anticipated or desired rate. Accordingly, VBA 100 may adjust the regimen, e.g., by recommending another product or referring the user to a specialist. As another example, VBA 100 may have recommended a particular hair care product, the efficacy of which may be determined from the amount of brushing required to smooth the user's hair, such as by the "smart" hairbrush discussed above. Other examples of the feedback will be apparent from this disclosure.

User/expert input and diagnostics 112 may include photographic images (uploaded to VBA client interface 114 from, for example, the user's photo library, taken within VBA client interface 114, automatically detected self-portraits (selfies) from the user's library, links to photographic images that are tagged in the client's social media; user-input habits from questions (e.g. smoking, alcohol, sleeping); user-input profile questions (e.g. ethnicity, skin type, preferences); user-input preferences regarding habits and products (e.g. "I didn't like this product because the texture was too sticky" or "telling me to eat less salt to keep my skin hydrated won't work because I need to eat more salt to prevent myself from fainting"); user-input diet; other service diet tracking (e.g. syncing with API from third party fitness tracking portals like MyFitnessPal); purchasing habits (e.g. credit card, etc.) to tie into other habits (like skin care product usage or how often you buy cigarettes to deduce the user's smoking frequency); social media profile overview (e.g. aggregating a user's likes, photos, uploads, interactions, etc.) to determine the user's "style" and "maintenance level" (e.g. beauty addict vs low maintenance lumberjack) automatically; public website product reviews linked with consumer type to recommend relevant products to the user's profile; public website product reviews linked with consumer type to recommend relevant products to the user's profile; product database with metadata about brand, claims, ingredients, efficacy levels, target customers, year developed, etc.

Diagnostic devices 120 may include third party, possibly proprietary connected environment devices (e.g., Nest); third party, possibly proprietary connected environment APIs (e.g. weather.com for UV index and pollution index in your location); third party, possibly proprietary connected personal health devices (e.g., connected scale, Fitbit); third party, possibly proprietary connected habits devices (e.g., Fitbit for exercise or Sense for sleep); device-input diet (e.g. connected kitchen scale or connected to food ordering service like Blue Apron), personal health devices (e.g. My UV Patch); commercial expert diagnostic devices (e.g. diagnoses taken at the counter like skin color with Le Teint Particular); commercial beauty diagnostic devices (e.g. Withings Hair Brush, Facefacts, NanoEnTech).

Platform resources 118 may include GPS tracking of a user's location to link with location API data; personal calendar; photographic images from camera, etc.

Output devices 130 may be targets that implement a service or product utilized by VBA 100 to achieve a desired goal. For example, output devices 130 may include a connection to traditional e-commerce to place product orders for the user through traditional services (e.g. Amazon, Ulta, Sephora). Such services may have products sent directly to the user's doorstep upon request or may automatically send the product to the user's doorstep via an automatically detected subscription service. Another output device 130 may connect to new e-commerce portal to order customized products based on the user's profile (e.g. customized serums or foundations developed personally for the user through a factory (e.g., Fablab) and delivered to your doorstep). Another output device 130 may be a calendar that tracks salon/spa/doctor appointments and, in certain embodiments, may initiate such appointments.

Diagnoses outputs 142 may include skin care diagnosis through imaging, instrumental measurements (occlusive water loss, conductance, etc.), and expert (dermatologist) advice, hair care diagnosis, etc.

Recommendation output type 144 may include skin care products and routines (routines can include the combination of products in certain orders or with certain actions, can be separate from products e.g., "wash with cold water", and can include lifestyle habits recommended e.g., "reducing alcohol consumption by 1 glass each outing will rehydrate your skin visibly by 30%"); hair care recommendations (can include specific products, product ordering, actions/education with products, actions separate from products, and lifestyle habits); hair styling recommendations (can include specific products, product ordering, actions/education with products, actions separate from products, and lifestyle habits); makeup recommendations (can include specific products, product ordering, actions/education with products, actions separate from products, and lifestyle habits); dermatologist/aesthetician/spa treatment recommendations (can include specific products, product ordering, timing of treatments, specific treatments to implement, specific practitioners to see based on the user's profile/preferences, etc.).

VBA 100 may provide coaching 146 by which a user can receive instructions/advice on how to achieve a particular goal. Coaching 146 may include video instruction or interactive coaching through a live or virtual advisor. VBA 100 may connect the user (via video chat or voice chat) with an expert (dermatologist, cosmetologist, aesthetician, hair stylist, makeup artist) for on-demand or system-triggered expert advice.

Auditioning 148 is an interactive process by which a user undergoes a particular regimen and feedback indicates how the regimen is progressing (either positively or negatively). For example, if a user uses a particular wrinkle cream to reduce crow's feet, as recommended by VBA 100, subsequent image analysis or other user input may determine that the wrinkle cream is not as effective as hoped. Auditioning 148 may then recommend additional or alternative products and/or techniques. Additional feedback may then determine whether the revised regimen is adequate or whether additional steps, such as recommending a dermatologist, are required. The process may continue until user feedback indicates that the regimen is having desired effects. It is to be understood that auditioning 148 works in conjunction with machine learning described herein.

Other services provided by VBA 100 may historical comparison e.g., "one year ago today, your skin was much more dry than it is right now. Given that the environment isn't that different, you can be pretty sure that your moisturizer is doing the trick!"

Figure 2:
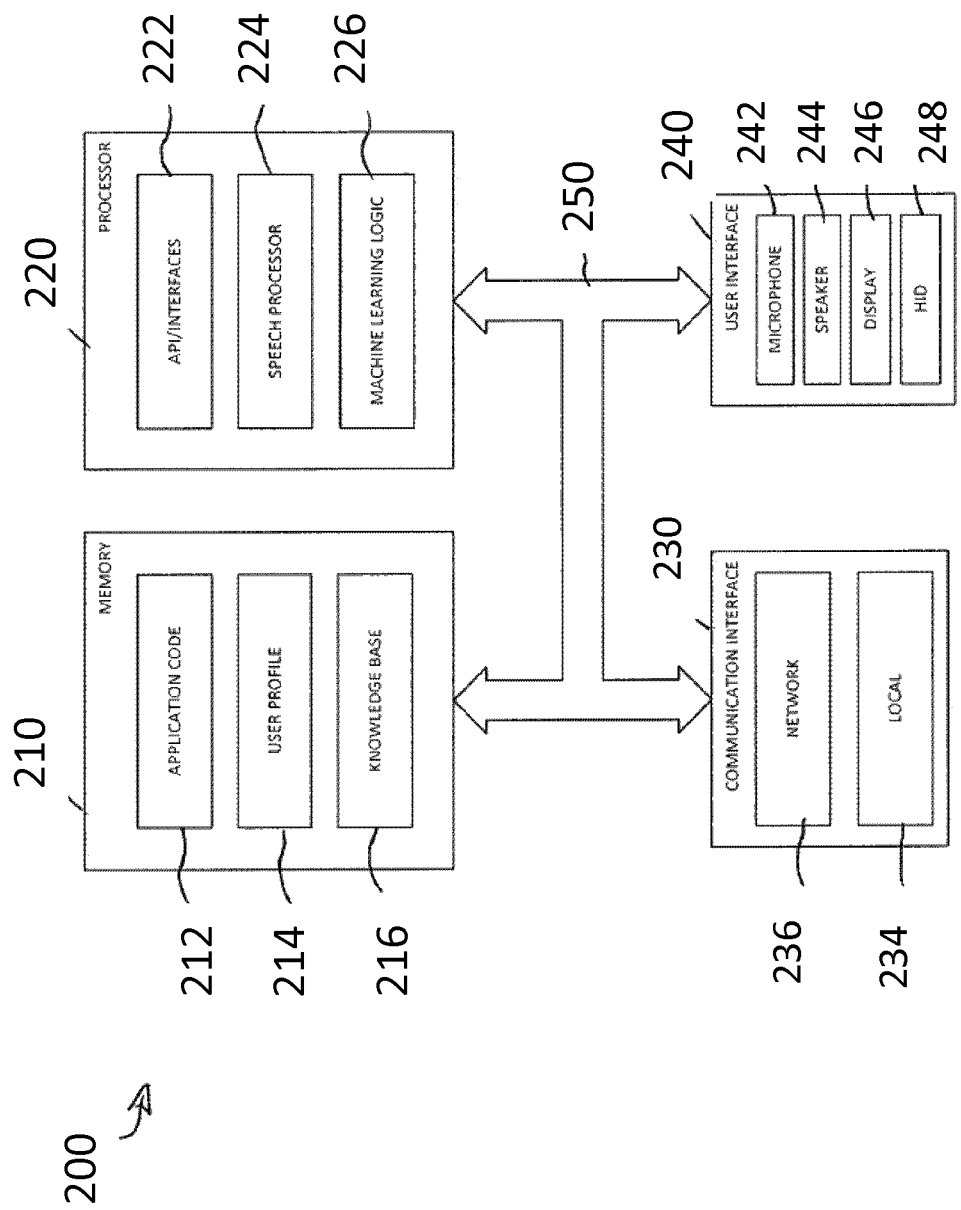
FIG. 2 is a schematic block diagram of a system configuration by which the present general inventive concept can be embodied.

FIG. 2 is a schematic block diagram of a system 200 by which the present invention can be embodied. It is to be understood that the illustration for purposes of description and is not intended as an electrical schematic. Example system 200 includes a memory 210, a processor 220, a communication interface 230 and a user interface 240 interconnected and communicatively coupled through a bus 250. It is to be understood that while the components in FIG. 2 are illustrated as being singular and discrete, such is for explanation purposes only. Each of memory 210, processor 220, communication interface 230, user interface 240 and bus 250 may comprise multiple such components and/or circuits to implement the invention embodiments. For example, processor 220 may comprise processing circuitry on a server (not illustrated) connected to a network as well as circuitry local to, say, user interface 240. When so embodied, bus 350 may include suitable circuitry to afford communications over that network. Alternatively, system 200 may reside on a single device using onboard equipment to implement system 200. Upon review of this disclosure, those having skill in the relevant arts will recognize numerous system configurations and data processing techniques that can be implemented to realize embodiments of the present invention without departing from the spirit and intended scope thereof.

Memory 210 in FIG. 2 represents one or more storage circuits that store code and/or data on behalf of system 200. Memory 210 may be implemented by any quantity of any type of conventional or other memory or storage device, and may be volatile (e.g., RAM, cache, flash, etc.), or non-volatile (e.g., ROM, hard-disk, optical storage, etc.), and include any suitable storage capacity. Memory 210 may be constructed or otherwise configured to store application code 212 for various applications including those associated with VBA 100, a user profile 214 that indicates user ground truth, preferences, etc. and a knowledge base 216 that stores information to carry out the tasks of VBA 100.

In FIG. 2, processor 220 represents one or more processing circuits that carry out processing operations of the present invention. The processing circuits may be microprocessors, microcontrollers, systems on a chip (SOCs), or other fixed or programmable logic, that executes instructions for process logic stored in memory 210. The processor circuits may themselves be multi-processors, and have multiple CPUs, multiple cores, multiple dies comprising multiple processors, etc.

Figure 3:
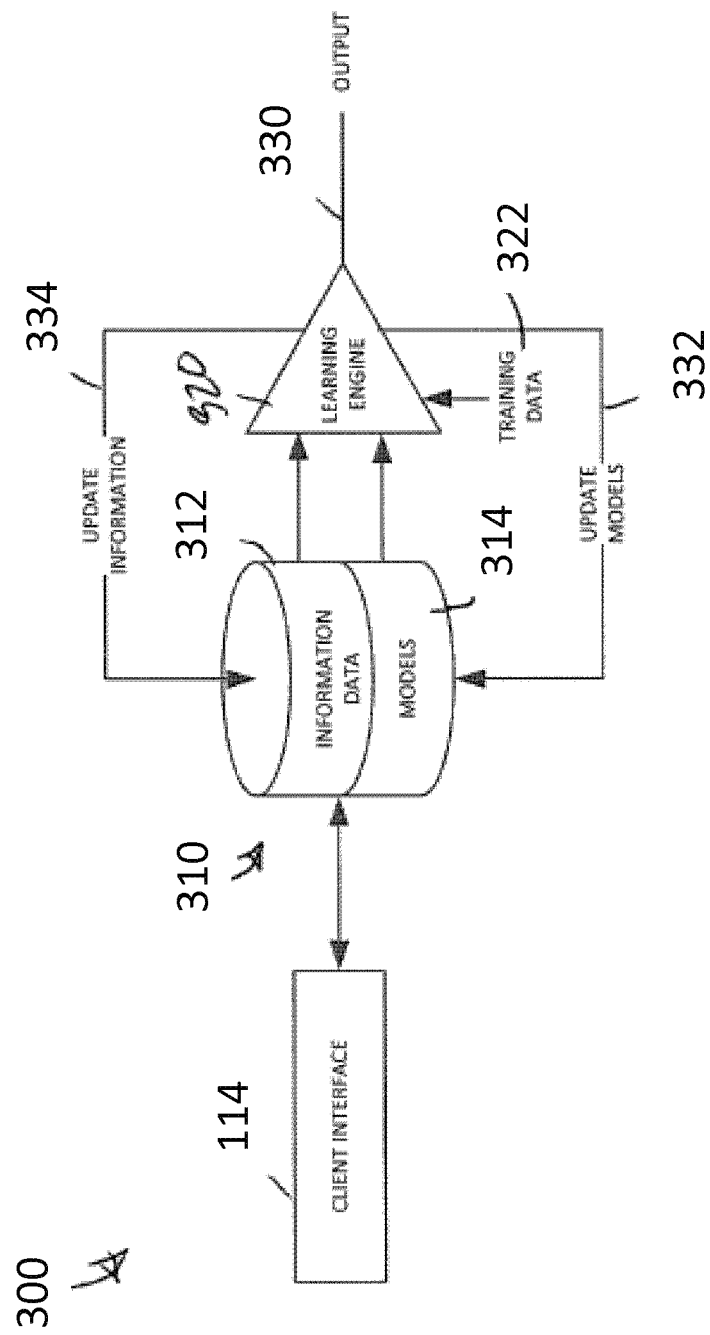
FIG. 3 is a conceptual flow diagram of machine learning that can be utilized in conjunction with the present general inventive concept.

Processor 220 may be constructed or otherwise configured to, among other things like executing application code 212, implement an application programming interface (API) and other interfaces like VBA client interface 114, a speech processor 224 to both decode speech from the user and synthesize speech to a user, and machine learning logic 226, such as that to implement the machine learning described with reference to FIG. 3.

Exemplary communication interface 230 represents one or more communication circuits that carry out communications with remote devices through, for example, network interface 232, and with local devices through, for example, local interface 234. Each of network interface 232 and local interface 234 may include wired electrical interfaces and/or wireless electrical interfaces to carry out embodiments of the invention. Communication interface 230 may be compatible with local and wide area networks, personal area networks, etc., and may be constructed or otherwise configured to interface with the smart devices described above.

User interface 240 represents circuitry by which a user interacts with system 200, e.g., a microphone 242, a speaker 244, a display 246 and one or more human interface devices (HIDs) 248. HIDs 248 may include a mouse, keyboard, touch screen, etc. In certain embodiments, user interface 240 is implemented on a smartphone or other device that includes onboard instruments (camera, GPS receiver, accelerometers, etc.; not illustrated) that can be used as additional input/output.

Certain embodiments of the invention implement machine learning; FIG. 3 is a flow diagram illustrating an exemplary machine learning process 300. Process 300 avails itself of a knowledge base 310, which may be configured to store information data 312 and models 314, and a machine learning engine 320. Information data 312 represent human knowledge encoded in machine-readable form and may include user profile data. As such, information data 312 may include text, imagery, audio, video, hyperlinks, information on accessing public/private APIs, etc. that convey a particular meaning to a human user. Accordingly, information data 312 may include metadata by which that meaning is conveyed through a machine. Models 314 may be machine executable instructions that interpret and/or transform the information data 312 (and associated metadata) into new information data 312 (and associated metadata). In certain embodiments of the invention, models 314 are constructed or otherwise configured to mimic a human health and beauty advisor based on the user's profile 214 and knowledge in information data 312 that are relevant to a particular user query or action.

Learning engine 320 performs data analysis, data transformation, etc. of information data 312 based on models 314 to produce an output 330. Output 330 may include images, videos, text, voice, scheduled appointment times, connections to devices (e.g., via a unique QR code on the user's smartphone that reveals the user's profile sufficiently to instruct a countertop device (e.g., DOSE) to create custom serums or to send the user's measured skin tone from a countertop device (e.g., Le Teint Particular) to be stored in the user's profile once taken) in addition to those output types described above.

Models 314 may be trained by learning engine 320 on training data 322 to produce output 330 that mimics that of a human. Such training may involve updating models 314, as illustrated at 332, such as by modifying certain weights embedded in one or more models 314. During non-training activity, learning engine 320 may be provided or may otherwise gather relevant information data 312 and the appropriate models 314 to generate hypotheses and to determine whether the hypotheses fit with modeled behavior. Such action may lead to new information data, which may be added to knowledge base 310 as illustrated at 334. User and other feedback through client interface 114 may corroborate or dispute hypotheses on output 330 and learning engine 320 may provide model updates 332 based on the feedback. Learning engine 320 may deploy one or more learning techniques including, but not limited to, decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning and learning classifiers. Those having skill in artificial intelligence and machine learning will recognize numerous techniques that can be used in conjunction with the present invention without departing from the spirit and intended scope thereof.

Figure 4:
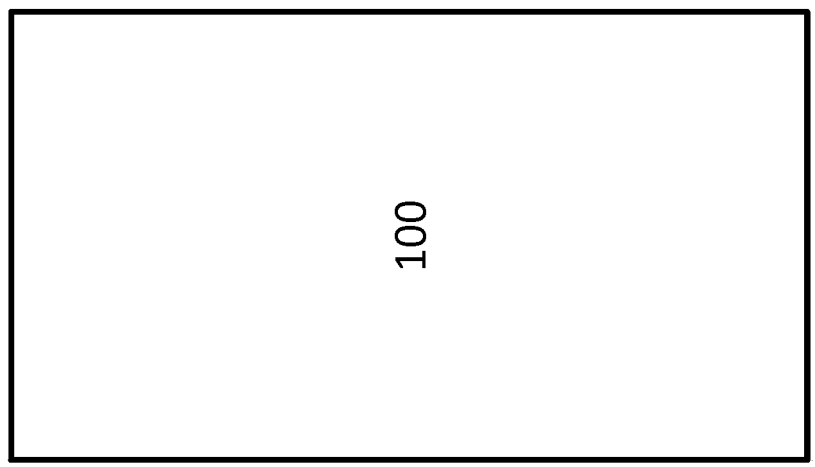
FIG. 4 illustrates two types of events which trigger a response from a virtual beauty assistant according to an embodiment.
Figure 4:
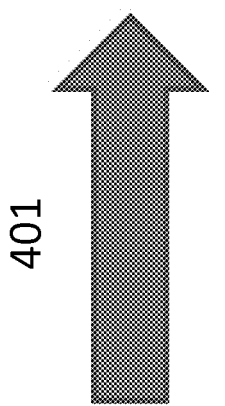
Figure 4:
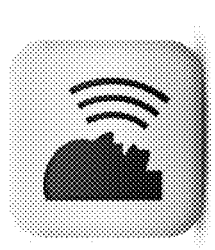
Figure 4:
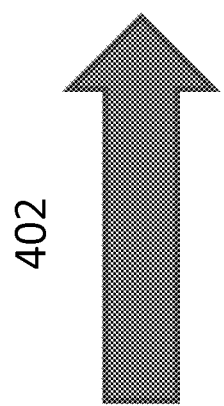
Figure 4:
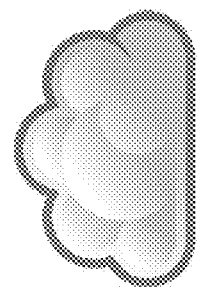
Figure 5:
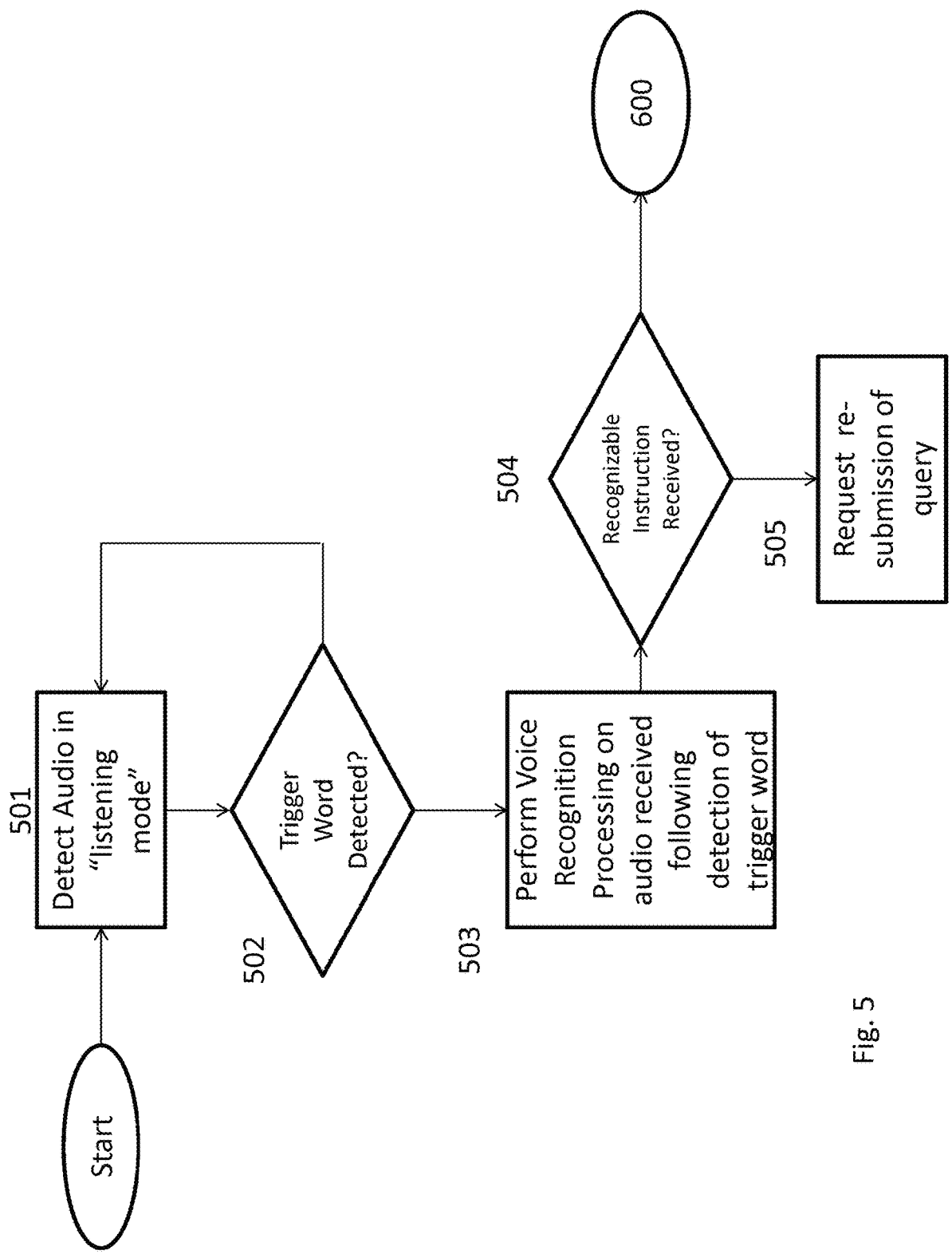
FIG. 5 shows a flowchart of a process performed by the virtual beauty assistant according to an embodiment.

In general, there are two types of events which trigger action by the VBA 100 as shown in FIG. 4. For instance, there are user-initiated actions 401 and there are automated actions 402 based on a predetermined schedule, history information, or trigger received over the network. FIG. 5 shows an example of an algorithm performed by the circuitry of the VBA 100.

As an example of a user-initiated action 401, the user may query the VBA 100 for specific advice as was described above. In other words, in response to the user query, the VBA 100 is able to provide a personalized response based on intelligently combining information taken from (i) a device which has directly sensed the user characteristic (in this example, a device which has tracked the user's sleep patterns), (ii) a previously provided user input of personal information (insomniac tendencies), and (iii) general available information that matches the user's needs (such as a commercially available eye cream and pre-existing coaching advice on how best to apply the eye cream).

As an example of an automated action 402 provided by the VBA 100, the VBA 100 "notices" is awake and performing a beauty routine. This action of noticing or detecting that the user is awake may be based on a proximity detector on the VBA 100, detection of audible voice sounds near the device, or based on the user turning on and activating one of the devices which is wireless connected with the VBA 100 (such as the smartphone or cosmetic appliance).

Figure 6:
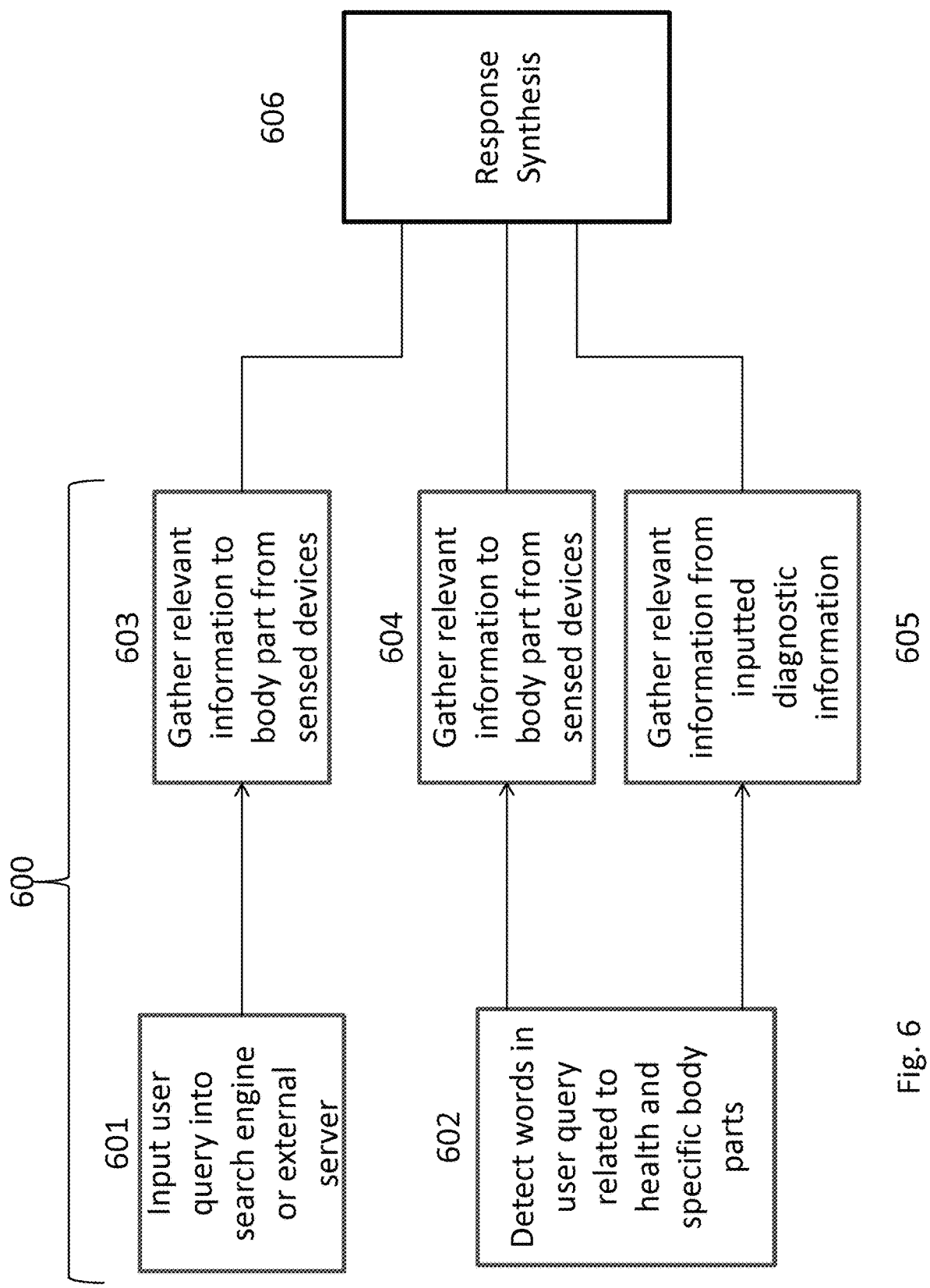
FIG. 6 shows an example of an information gathering stage performed by the virtual beauty assistant according to an embodiment.

FIGS. 5-6 show examples of processes (algorithms) implemented by the VBA 100 to achieve the exemplary results noted above.

FIG. 5 shows a process 501 for initially receiving a voice command from the user in order to process a user-initiated action, such as 301 above. In step 501, the VBA 100 is in the low-powered "listening mode." In step 502, the VBA 100 uses voice and speech recognition to detect of a particular command word has been spoken. In the present example, the pre-configured command word is "Violet." If the command word is detected, the process proceeds to step 503, otherwise the process returns to listening mode in step 501. Following the detection of the command word in step 502, the device then performs detailed voice recognition processing on any words spoken by the user subsequent to the detection. The statements of the user are translated into a recognizable instruction by the VBA 100. Such conventional voice recognition technology is understood in the art and will not be discussed in detail. In step 504, if a recognizable instruction is detected, the process will proceed to an information gathering stage 505. Otherwise, if a recognizable instruction is not detected, then the VBA 100 may audible ask the user to repeat the question, for example, by asking "I'm sorry, I didn't understand that, please repeat or rephrase your question."

FIG. 6 shows an example of an information gathering stage 605 performed by the VBA 100. In step 601, the user query may be inputted into a search engine to gather generally available information related to the user query. In other words, if the user question is "How to avoid dark circles?", this entire query may be directly inputted into a database or Internet search engine to gather information related to the query.

In step 602, individual words in the query may be extracted and parsed by the VBA 100. For instance, the phrase "dark circles" may be extracted and determined to be related to the features "eyes", "skin", and "sleep" based on predetermined mapping of these words to the original phrase "dark circles."

In step 604 information related to the user's or expert's inputted information is gathered based on the extracted words, or the mapped words related to the extracted words. For instance, sleep history, conditions, or habits related to the extracted terms are pulled out.

In step 605, information detected from any of the sensed devices connected to the VBA 100 are gathered based on the extracted words, or the mapped words related to the extracted words.

After all of the information is gathered, the information is forwarded for performing response synthesis 606 which will determine the appropriate outputted response, such as the examples of different outputs described above.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable medium may be, for example, but is not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a solid state disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a phase change memory storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, e.g., an object oriented programming language such as Java, Smalltalk, C++ or the like, or a conventional procedural programming language, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

It is to be understood that the software for the computer systems of the present invention embodiments may be implemented in any desired computer language and could be developed by one of ordinary skill in the computer arts based on the functional descriptions contained in the specification and flow charts illustrated in the drawings. By way of example only, the software may be implemented in the C++, Java, P1/1, Fortran or other programming languages. Further, any references herein of software performing various functions generally refer to computer systems or processors performing those functions under software control.

The computer systems of the present invention embodiments may alternatively be implemented by any type of hardware and/or other processing circuitry. The various functions of the computer systems may be distributed in any manner among any quantity of software modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.).

The foregoing examples are illustrative of certain functionality of embodiments of the invention and are not intended to be limiting. Indeed, other functionality will be described below and other possible use cases will be apparent to the skilled artisan upon review of this disclosure.

The invention claimed is:

1. An apparatus comprising:
    circuitry configured to accept data indicative of at least one health or beauty state of a user from multiple types of diagnostic devices, including a hairbrush equipped with sensors and a detector that measures sleep patterns; and
    a microphone configured to receive a vocal query from the user regarding the least one health or beauty state of a user;
    wherein the circuitry is further configured to
        collect the accepted data from at least one of the multiple types of diagnostic devices based on associating a type of data sensed or measured from the at least one of the multiple types of diagnostic devices and a health or beauty issue included in words extracted from the vocal query from the user;
        convey the collected accepted data to machine learning models and to receive a regimen recommendation from the machine learning models; and
    a user interface circuit to audibly present the regimen recommendation to the user via a speaker,
    wherein when the vocal query from the user regards an appearance of the user's eyes the circuitry is configured to associate the vocal query from the user with the detector that measures sleep patterns, and
        (i) when the accepted data from the detector that measures sleep patterns indicates that the user is getting an amount of sleep that is predetermined as insufficient, the regimen recommendation includes a recommendation of obtaining more sleep for treating the appearance of the user's eyes, (ii) when the accepted data from the detector that measures sleep patterns indicates that the user is getting a sufficient amount of sleep, the regimen recommendation includes a recommendation of applying a particular cosmetic product for treating the appearance of the user's eyes.

2. The apparatus of claim 1, wherein the circuitry is further configured to accept input data indicative of an efficacy of the regimen.

3. The apparatus of claim 2, wherein the input data indicative of the efficacy of the regimen is accepted from the at least one of the multiple types of diagnostic devices.

4. A method, implemented by circuitry of an apparatus, comprising:
   accepting data indicative of at least one health or beauty state of a user from multiple types of diagnostic devices, including a hairbrush equipped with sensors and a detector that measures sleep patterns;
   receiving, by a microphone, a vocal query from the user regarding the least one health or beauty state of a user;
   collecting the accepted data from at least one of the multiple types of diagnostic devices based on associating a type of data sensed or measured from the at least one of the multiple types of diagnostic devices and a health or beauty issue included in words extracted from the user's vocal query from the user;
   conveying the collected accepted data to machine learning models and to receive a regimen recommendation from the machine learning models; and
   audibly presenting the regimen recommendation to the user via a speaker,
   wherein when the vocal query from the user regards an appearance of the user's eyes the method includes associating the vocal query from the user with the detector that measures sleep patterns, and
   (i) when the accepted data from the detector that measures sleep patterns indicates that the user is getting an amount of sleep that is predetermined as insufficient, the regimen recommendation includes a recommendation of obtaining more sleep for treating the appearance of the user's eyes,
   (ii) when the accepted data from the detector that measures sleep patterns indicates that the user is getting a sufficient amount of sleep, the regimen recommendation includes a recommendation of applying a particular cosmetic product for treating the appearance of the user's eyes.

5. The method of claim 4 further comprising accepting input data indicative of an efficacy of the regimen.

6. The method of claim 5 further comprising accepting the input data indicative of the efficacy of the regimen from the at least one of the multiple types of diagnostic devices.

* * * * *